US008295569B2

(12) United States Patent
Park et al.

(10) Patent No.: US 8,295,569 B2
(45) Date of Patent: Oct. 23, 2012

(54) METHOD AND SYSTEM FOR AUTOMATIC DETECTION AND MEASUREMENT OF MITRAL VALVE INFLOW PATTERNS IN DOPPLER ECHOCARDIOGRAPHY (75) Inventors: Jin-hyeong Park, Princeton, NJ (US); Shaohua Kevin Zhou, Plainsboro, NJ (US); John I. Jackson, Menlo Park, CA (US); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 786 days.

(21) Appl. No.: 12/481,861

(22) Filed: Jun. 10, 2009

(65) Prior Publication Data

US 2009/0310837 A1 Dec. 17, 2009

Related U.S. Application Data (60) Provisional application No. 61/060,866, filed on Jun. 12, 2008.

(51) Int. Cl.
*G06K 9/00* (2006.01)

(52) U.S. Cl. .................. 382/128; 382/203; 128/922

(58) Field of Classification Search .................. 382/128, 382/131, 203, 207, 227, 228; 128/922; 600/449, 600/450, 453, 454
See application file for complete search history.

(56) References Cited

U.S. PATENT DOCUMENTS

| | | | |
|---|---|---|---|
| 5,429,137 A | 7/1995 | Phelps et al. | 128/661.09 |
| 6,346,124 B1 | 2/2002 | Geiser et al. | 600/450 |
| 6,716,175 B2 | 4/2004 | Geiser et al. | 600/450 |
| 2006/0045347 A1 | 3/2006 | Xiao et al. | 382/190 |
| 2006/0074312 A1 | 4/2006 | Georgescu et al. | 600/437 |
| 2008/0069436 A1 | 3/2008 | Orderud | 382/154 |
| 2009/0010509 A1 | 1/2009 | Zhou et al. | 382/128 |
| 2009/0088640 A1* | 4/2009 | Park et al. | 600/453 |

OTHER PUBLICATIONS

Felzenszwalb, P., "Representation and Detection of Deformable Shapes", IEEE Trans. PAMI, 2005.
Liu, L., et al., "Deformable Shape Detection and Description Via Model-Based Region Grouping", IEEE Trans. PAMI, 1999.
Georgescu, B., et al., "Database-Guided Segmentation of Anatomical Structures with Complex Appearance", Proc. of CVPR (2005), pp. 429-436.

* cited by examiner

*Primary Examiner* — Andrew W Johns (57) ABSTRACT

A method and system for segmentation of mitral valve inflow (MI) patterns in Doppler echocardiogram images is disclosed. Trained root detectors are used to detect left root candidates, right root candidates, and peak candidates in an input Doppler echocardiogram image. Two global structure detectors, a single triangle detector for non-overlapping E-waves and A-waves and a double triangle detector for overlapping E-waves and A-waves, are used to detect single triangle candidates and double triangle candidates based on the left root, right root, and peak candidates. A shape profile is used to determine a shape probability for each of the single triangle candidates and each of the double triangle candidates. The best single triangle candidate and the best double triangle candidate are selected based on shape probability and detection probability. One of the best single triangle candidate and the best double triangle candidate is selected as the final segmentation result based on a shape probability comparison.

29 Claims, 5 Drawing Sheets

METHOD AND SYSTEM FOR AUTOMATIC DETECTION AND MEASUREMENT OF MITRAL VALVE INFLOW PATTERNS IN DOPPLER ECHOCARDIOGRAPHY

This application claims the benefit of U.S. Provisional Application No. 61/060,866, filed Jun. 12, 2008, the disclosure of which is herein incorporated by reference.

BACKGROUND OF THE INVENTION

The present invention relates to Doppler echocardiography, and more particularly, to detection and measurement mitral valve inflow patterns in Doppler echocardiography.

Doppler echocardiography is widely used in clinical practices to assess heart valve functionality as the blood velocity is recorded. The conventional workflow of Doppler analysis requires manual tracing of the envelopes of acquired Doppler spectra. Once the envelopes of the acquired Doppler spectra are traced, clinically relevant measurements are computed based on the traced envelopes. The manual tracing is a main bottleneck of the workflow. Accordingly, a method for automatically detecting envelopes in the Doppler spectra is desirable.

Figure 1A:
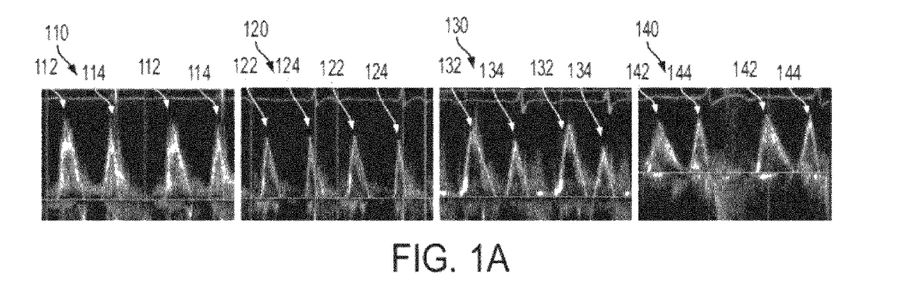
FIGS. 1A and 1B illustrate exemplary mitral valve inflow (MI) Doppler spectra.
Figure 1B:
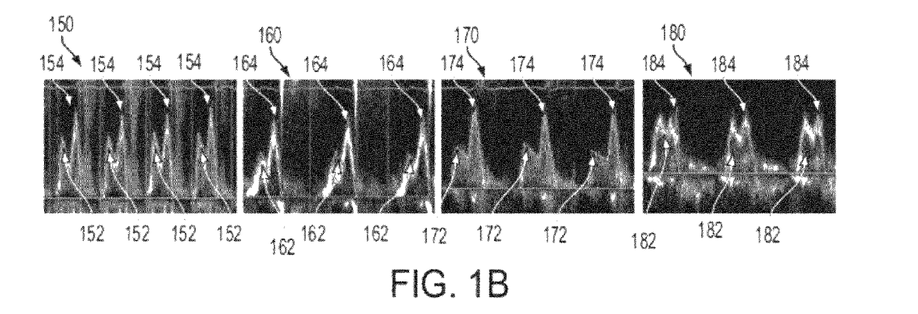

Mitral valve inflow (MI) patterns and measurements have been studied extensively as indices of left ventricular diastolic function. FIGS. 1A and 1B illustrate exemplary MI Doppler spectra with expert annotated envelopes overlaid thereon. The MI pattern, which occurs in the ventricular diastole phase, typically includes an "early" wave (E-wave) and an "atrial" wave (A-wave). For normal hearts, the E-waves and A-waves do not overlap each other and the E-wave is higher than the A-wave. FIG. 1A illustrates exemplary MI Doppler echocardiography images 110, 120, 130, and 140 in which the E-waves 112, 122, 132, and 142 do not overlap with the A-waves 114, 124, 134, and 144. For diseased hearts, the following can occur: the E-waves and the A-waves can overlap depending on the heart diseases; the E-wave can be lower than or at the same height as the A-wave; or only the E-wave may be present with no A-wave. FIG. 1B illustrates exemplary MI Doppler echocardiography images 150, 160, 170, and 180 in which the E-waves 152, 162, 172, and 182, overlap with the A-waves 154, 164, 174, and 184. The above factors contribute significant variation in the envelope shape of MI Doppler spectra. In terms of image appearance, the variation is too large to apply conventional techniques, such as signal aliasing, difference in imaging setting, etc. for detecting the envelopes.

Some conventional approaches utilize image processing/filtering techniques, such as low-pass filtering, thresholding, and edge detection to attempt to automatically trace Doppler spectra envelopes. However, such techniques do not guarantee robustness in the presence of severe image artifacts.

BRIEF SUMMARY OF THE INVENTION

The present invention addresses detection of mitral valve inflow (MI) patterns in Doppler echocardiograph images. Embodiments of the present invention provide a probabilistic, hierarchical, and discriminant (PHD) framework for classifier based detection of MI spectra in Doppler echocardiograph images. Embodiments of the present invention explicitly handle overlapping E-waves and A-waves in MI Doppler spectra by separately detecting and segmenting non-overlapping E-waves and A-waves and overlapping E-waves and A-waves.

In one embodiment of the present invention, left root candidates, right root candidates, and peak candidates are detected in an input Doppler echocardiogram image using trained root detectors. Single triangle candidates and double triangle candidates are detected based on the left root, right root, and peak candidates using global box detectors. This results in a detection probability for each of the single triangle candidates and each of the double triangle candidates. A shape probability is determined for each of the single triangle candidates and each of the double triangle candidates. The best single triangle candidate and the best double triangle candidate are selected based on shape probability and detection probability. One of the best single triangle candidate and the best double triangle candidate is selected as the final segmentation result based on a shape probability comparison.

These and other advantages of the invention will be apparent to those of ordinary skill in the art by reference to the following detailed description and the accompanying drawings.

DETAILED DESCRIPTION

The present invention is related to detection and measurement of mitral valve inflow (MI) patterns in Doppler echocardiography images. Embodiments of the present invention are described herein to give a visual understanding of the MI pattern detection method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

U.S. patent application Ser. No. 12/214,339, filed Jun. 18, 2008, which is incorporated herein by reference, discloses probabilistic, hierarchical, and discriminative (PHD) framework for detection and segmentation of deformable anatomic structures in medial images. This method was successfully applied for automatically tracing the envelopes of three Doppler flow types including MI. In this application, a triangle representation is used to model the MI envelope. This representation has inherent difficulty when dealing with severely overlapping E-waves and A-waves, rendering the missing triangle roots, which are often seen in the spectra of diseased hearts.

Embodiments of the present invention utilize a PHD framework for detection of MI envelopes in Doppler echocardiography images. However, unlike in U.S. patent application Ser. No. 12/214,339, embodiments of the present invention explicitly handle overlapping E-waves and A-waves in MI Doppler spectra by separately detecting and segmenting non-overlapping E-waves and A-waves and overlapping E-waves and A-waves. The non-overlapping case is formulated as a problem of a single triangle detection/segmentation, which means that E-waves and A-waves are treated as the same object with a triangle shape. In the overlapping case, a pair of overlapping E and A-waves are detected/segmented.

In order to achieve automatic detection and segmentation of the target deformable objects (i.e., MI envelopes), embodiments of the present invention first employ a series of trained detectors to anchor the location of the objects, and then utilizes shape information to segment the deformable object. A single triangle object represents an isolated E-wave or A-wave, and a double triangle object represents a pair of overlapping E and A-waves. A single triangle model has three points: a left root, a right root, and a peak. A double triangle model has five points, a left root, a right root, a left peak, a right peak, and an intersection point. Based on the observation that both the single and double triangle models share the left root, right root, and peak(s), three part detectors are trained: left root detector LRD), right root detector (RRD), and peak detector (PKD). Although the double triangle has two peaks, these peaks can be pooled together during training according to an advantageous embodiment of the present invention. In addition to the root detectors, two global box detectors are trained: a single triangle detector (STD) and a double triangle detector (DTD). These detectors are organized in a hierarchical manner to efficiently prune the search space down to a set of most promising candidates for both single and double triangle objects. Each candidate is associated with a posterior detection probability $P_D(\Theta|I)$, where $\Theta$ is the shape model.

The above described detectors are organized into a two-layer hierarchy. The first layer comprises the LRD, RRD, and PKD, which output independent candidates for the left root, right root, and peak. The second layer comprises the STD and DTD. Each detector (LRD, RRD, PKD, STD, and DTD) in the detector hierarchy can be a binary object detector trained as a probabilistic boosting tree (PBT). The PBT trains a binary decision tree, with each node of the tree being a strong classifier that combines multiple weak classifiers via a discriminant boosting method. Since the weak classifiers can be based on Haar-like local rectangle features whose rapid evaluation is enabled by an integral image, the PBT operates as a feature selector. The PBT also has early exits for fast negative rejection. The PBT also allows exact computation of the posterior probability of a candidate being positive.

In order to train detectors in all layers of the progressive detector hierarchy as PBTs, positive and negative training samples must be generated. Positive training samples can be generated using ground truth annotation (with a slight perturbation). When generating negative training samples, the interaction between layers of the progressive detector hierarchy is taken into account, especially for the second layer (STD and DTD) of the hierarchy. For example, when generating positives and negatives for the second layer global box detectors (STD and DTD), the candidates with positive values (including false positives) that pass the first layer root detectors (LRD, RRD, and PKD) are used. This approach can reduce training complexity of STD and DTD by imposing search space constraints using the first layer root detectors.

Figure 2:
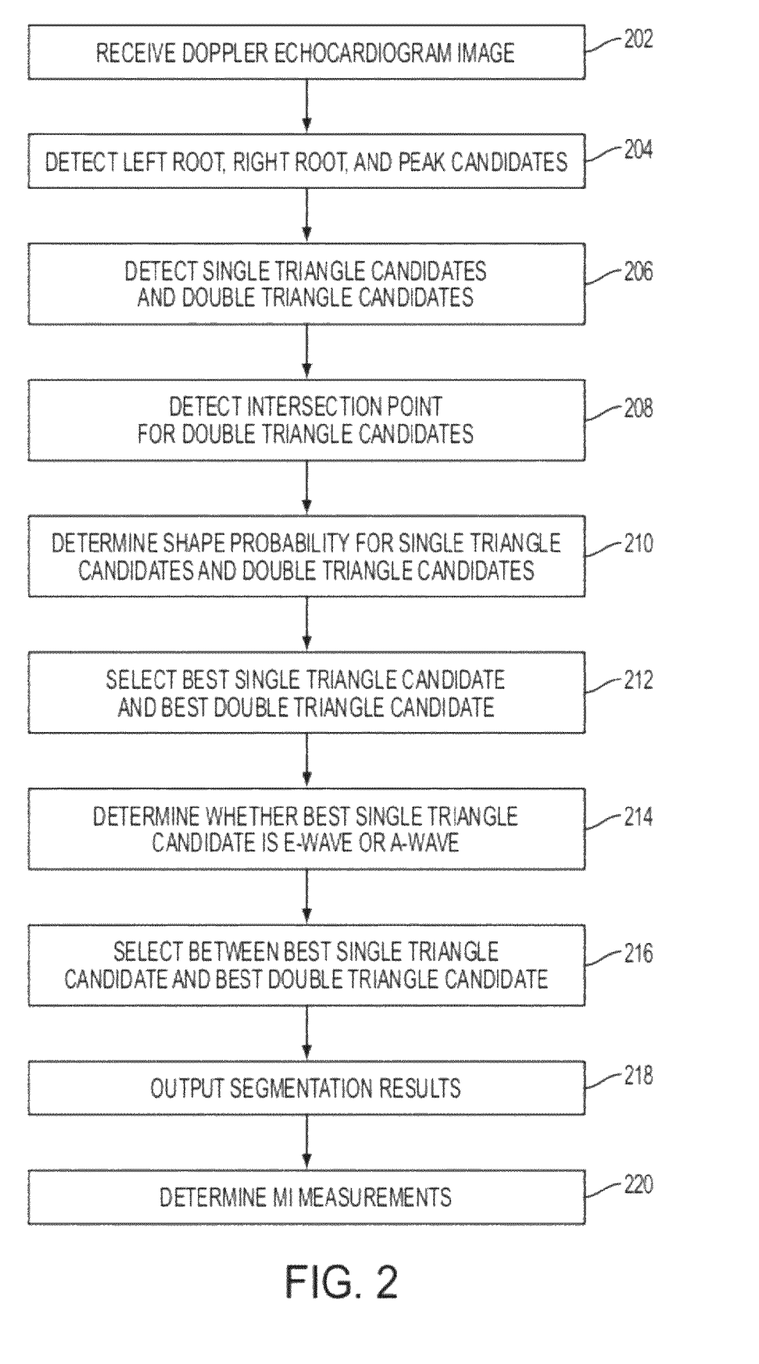
FIG. 2 illustrates a method for detecting MI patterns in a Doppler echocardiography image according to an embodiment of the present invention.

Once the detectors are trained, as described above, the detectors can be used in the detection and segmentation of MI patterns in an input Doppler echocardiography image. FIG. 2 illustrates a method for detecting MI patterns in a Doppler echocardiography image according to an embodiment of the present invention. It is to be understood that the method of FIG. 2 transforms Doppler echocardiography image data representing blood flow in a patient's heart to generate data representing mitral valve inflow (MI) for the patient. FIGS. 3A-3F illustrate exemplary Doppler echocardiogram images resulting from various steps of the method of FIG. 2. FIGS. 3A-3F are referred to herein while describing the method of FIG. 2.

Figure 3A:
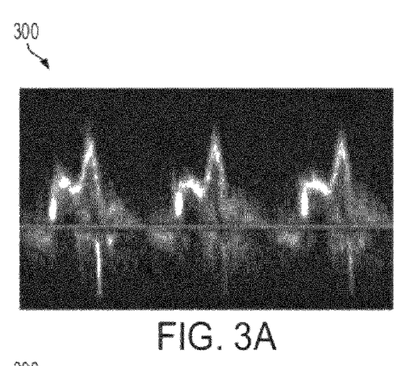
FIGS. 3A-3F illustrate exemplary Doppler echocardiogram images resulting from various steps of the method of FIG. 2.

Referring to FIG. 2, at step 202, an input Doppler echocardiogram image is received. The Doppler echocardiogram image can be received from a medical imaging device, such as an ultrasound device. It is also possible that the Doppler echocardiogram image is received by loading a previously stored Doppler echocardiogram, for example from a storage or memory of a computer implementing the method or from a computer readable medium. FIG. 3A shows an exemplary input Doppler echocardiogram image 300.

Figure 3B:
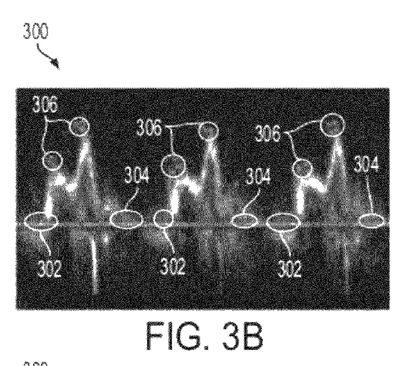

At step 204, left root, right root, and peak candidates are detected in the input image using trained root detectors. As described above, the LRD, RRD, and PKD are trained to detect the left root, right root, and peak(s), respectively. These parameters detected by the first layer detectors (LRD, RRD, and PKD) are used by both the single triangle model and the double triangle model. Each detector is trained based on training data including single triangle samples and double triangle samples. Each detection carries a detection probability. For example, the LRD outputs the posterior probability of being a left root object $O_{LR}$ given an input image I and a hypothesized location $\theta_{LR}$, which is denoted by $P(O_{LR}|I,\theta_{LR})$. The RRD and PKD output similar probabilities of locations in the input image being a right root object and a peak object, respectively. FIG. 3B shows left root candidates 302, right root candidates 304 and peak candidates 306 detected in the input image 300 by the first layer detectors (LRD, RRD, and PKD).

At step 206, candidate boxes for single triangle candidates and double triangle candidates are detected using the trained global box detectors based on the detected left root, right root, and peak candidates. As described above, the STD is a box detector trained to detect single triangle candidates and the DTD is a box detectors trained to detect double triangle candidates. As described above, the detectors are organized into a two-layer hierarchy. The first layer detectors (LRD, RRD, and PKD) output independent candidates for the left root, right root, and peak. The STD further verifies if a particular combination of a left root, a right root, a peak point from the candidates for a valid E-wave or A-wave. If the combination passes the STD (i.e., has a high enough posterior probability), the two root points and the peak point form a trace of a single triangle envelope. Such combinations with the highest posterior probability are kept as the single triangle candidates. The DTD verifies if a particular combination of a left root, a right root, and two peak points that lie in between the left and right roots forms a valid double triangle pattern. The combinations with the highest probability are kept as the double triangle candidates. However, such double triangle candidates only have four parameters, with the intersection point of the E-wave deceleration line and the A-wave acceleration line missing. This parameter must be estimated for these double triangle candidates.

A target object O parameterized by $\Theta$ consists of M parts $O=\{O_1, O_2, \ldots, O_M\}$ with part $O_i$ parameterized by $\theta_i$. According to an embodiment of the present invention, two target objects are defined: (i) a single triangle object with a left root (LR), a right root (RR), and a peak point (PK), i.e., $O_{ST}=\{O_{LR}, O_{RR}, O_{PK}\}$ and $\Theta_{ST}=\{\theta_{LR}, \theta_{RR}, \theta_{PK}\}$; and (ii) a double triangle object with a LR, a RR, an E-wave peak point (EPK), and an A-wave peak point (APK), i.e., $O_{DT}=\{O_{LR}, O_{RR}, O_{EPK}, O_{APK}\}$ and $\Theta_{DT}=\{\theta_{LR}, \theta_{RR}, \theta_{EPK}, \theta_{APK}\}$ The PHD framework assumes conditional independence among the parts of the global structure. For the single triangle object, the detection probability for a single triangle candidate in the input image is defined as:

$$P_D(\Theta_{ST}|I) \equiv \prod_{a \in A} P(O_a|I, \theta_a) P(O_{ST}|I, \Theta_{ST}), \quad (1)$$

where A={LR, RR, PK}. A similar detection probability $P_D (\Theta_{DT}|I)$ can be defined for the double triangle object. The conditional independence of assumption brings a computational advantage, in that if one of the detectors fails, the overall detection fails.

Figure 3C:
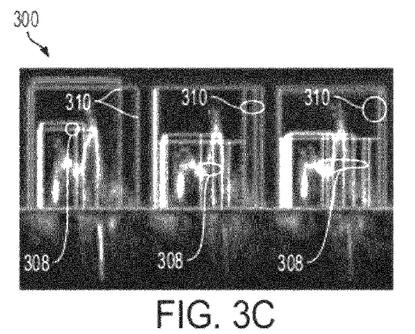

FIG. 3C shows single triangle candidate boxes 308 and double triangle candidate boxes 310 resulting detected in the input image 300 by the second layer detectors (STD and DTD). At step 208, an intersection point is detected in the double triangle candidates. Once a candidate box for a single triangle is identified, all of the single triangle parameters (left root, right root, and peak) are known, and the triangle shape is fully specified. However, this is not the case for a double triangle candidate, as the intersection point of the two overlapping triangles is still unknown. According to an advantageous embodiment of the present invention, a shape inference model can be used to determine the intersection point of the E-wave deceleration line and the A-wave acceleration line of a double triangle candidate. Given the training images and their corresponding shapes, a nonparametric regression function can be learned that gives a mapping from an image to its shape. In an advantageous implementation, the training images are the cropped double triangles with same image size, for example 100 pixels by 100 pixels. The shape of each cropped image is defined by the coordinates of the 5 points: one left root, one right root, two peaks, and the intersection point. The training of the shape inference model conducts a feature selection process.

Each image is represented by an over-complete set of features. The training data are first clustered in the shape space into several clusters. After training, a training image $I_j$, whose shape is $\Phi_j$, is represented by a feature vector $f_j$. Given an input image I, its corresponding feature vector f is first computed, then the trained nonparametric regression function is invoked to infer the shape $\Phi$:

$$\Phi = \frac{\sum_j \Phi_j k(f_j, f)}{\sum_j k(f_j, f)}, \quad (2)$$

where k is a kernel function. The shape $\Phi$ invoked for the input image is used to estimate the intersection point of the double triangle. The use of such a shape inference model is described in greater detail in B. Georgescu et al., "Database-Guided Segmentation of Anatomical Structures with Complex Appearance", Proc. Of CVPR (2005), pgs. 429-436, which is incorporated herein by reference.

Figure 3D:
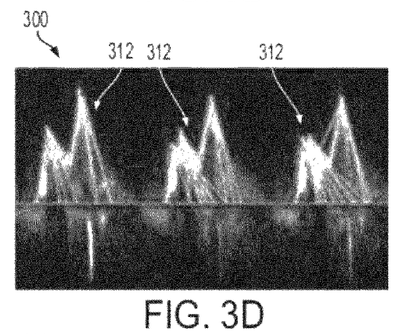

FIG. 3D shows double triangle candidates 312 resulting from applying a shape inference model to the double triangle candidate boxes 310 in order to find the intersection point between the E-wave deceleration line and the A-wave acceleration line.

At step 210, a shape probability is determined for each single triangle candidate and each double triangle candidate. To define the shape probability $P_S (\Phi|I)$, image evidence is used along the shape of each segmented envelope. Suppose the trace of the envelope has N discrete points, $\{s_i=(x_i,y_i)\}_{i=1}^N$, distributed with equal distance along the trace. For each point, $s_i$, a shape profile score $\psi_i$ is calculated based on the intensity gradients along the trace of the envelope. Let line $l_i$ be perpendicular to the tangent of a point $s_i$. Points on the line $l_i$ can be denoted by $\{s_{ij}=(x_{ij},y_{ij})\}_{j=i-\Delta}^{i+\Delta}$, where $\Delta>0$ and $s_i=s_{ij}$, and it can be assumed that $\{s_{ij}=(x_{ij},y_{ij})\}_{j=i-1}^{i-\Delta}$ corresponds to the outside of the contour and $\{s_{ij}=(x_{ij}, y_{ij})\}_{j=i+1}^{i+\Delta}$ corresponds to the inside of the contour. Then, the $i^{th}$ shape profile score can be defined as:

$$\psi_i = \sum_{j=1}^{i+\Delta} I(s_{ij}) - \sum_{i-\Delta}^{j=1} I(s_{ij}), \quad (3)$$

where $I(s_{ij})$ represents a pixel intensity at the location of $s_{ij}$. The shape probability is then defined using a Sigmoid function:

$$P_S(\Phi|I) \equiv \left[1 + \exp\left(-\gamma \sum_i \psi_i\right)\right]^{-1}, \quad (4)$$

where $\gamma>0$ is a pre-specified constant. Accordingly, a shape probability can be calculated for each single triangle candidate and for each double triangle candidate.

At step 212, a best single triangle candidate and a best double triangle candidate are selected based on the shape probability and the detection probability. By integrating both the detection posterior probability $P_D (\Theta|I)$ and the shape posterior probability $P_S (\Phi|I)$, for each of the single triangle candidates and for each of the double triangle candidates, the best single triangle candidate and the best double triangle candidate can be selected for each heart cycle among the cluster of detection results. Assuming that the detectors and shape profiles are independent of each other, which is a reasonable assumption because they are two heterogeneous models, the fused probability can be obtained for each candidate as:

$$P(\Theta,\Phi|I)=P_D(\Theta|I)P_S(\Phi|I). \quad (5)$$

This fused probability is calculated separately for each of the single triangle candidates and for each of the double triangle candidates. A best single triangle candidate is selected that locally maximizes the fused probability, and a best double triangle candidate is selected that that locally maximizes the fused probability.

Figure 3E:
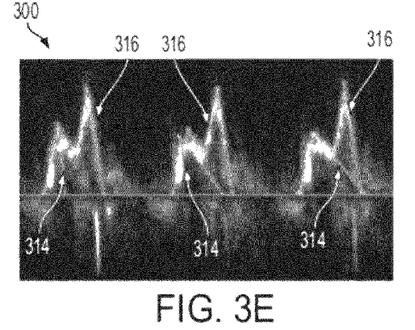

FIG. 3E shows a best single triangle candidate 314 and a best double triangle candidate 316 selected for each heart cycle.

At step 214, it is determined whether the best single triangle candidate is an E-wave or an A-wave. If the segmented envelope of the MI spectra is a single triangle object, the determination of whether the triangle represents and E-wave or an A-wave may be necessary for measurements of the MI spectra. This can be determined based on the End of Systole (ES) and End of Diastole (ED) lines given in the Doppler echocardiogram, because the E-wave appears first and the A-wave follows in the diastole period.

At step 216, the best single triangle candidate or the best double triangle candidate is selected based on a comparison of shape probability. In order to select between the best single triangle candidate and the best double triangle candidate, the shape probabilities are compared. This selection relies only on the shape probability because the detection probabilities from the two models (single triangle and double triangle) are heterogeneous. The selected model defines the segmentation result of the MI pattern in the Doppler echocardiogram image.

Figure 3F:
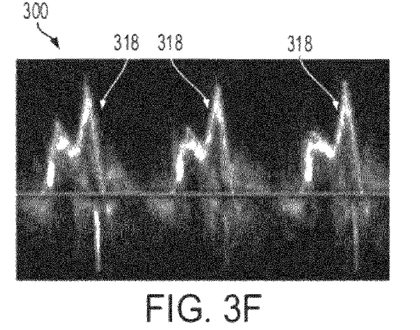

At step 218, the MI segmentation results are output. For example, the best single triangle model or best double triangle model that is selected in step 216 can be displayed on a display of a computer system. The segmentation results can also be output by storing the segmentation results, for example on a memory or storage of a computer system or on a computer readable medium. FIG. 3F shows segmented MI patterns 318. The segmentation results 318 shown FIG. 3F result from the selection of the best double triangle candidate 316 in FIG. 3E.

Figure 4A:
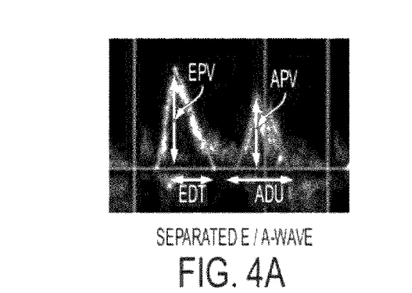
FIGS. 4A and 4B illustrate measurements calculated from segmented MI patterns.
Figure 4B:
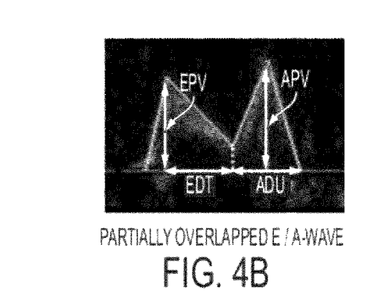

At step 220, MI measurements are automatically determined from the output MI pattern. Various MI measurements can be automatically determined from the segmented MI pattern. For example, the E-wave peak velocity (EPV), E-wave deceleration time (EDT), A-wave peak velocity (APV), and A-wave duration (ADU) are clinically relevant measurements that can be automatically calculated from the segmented MI pattern. FIGS. 4A and 4B illustrate measurements calculated from segmented MI patterns. FIG. 4A shows EPV, EDT, APV, and ADU measurements for non-verlapping E and A-waves and FIG. 4B shows EPV, EDT, APV, and ADU measurements for overlapping E And A-waves.

Figure 5:
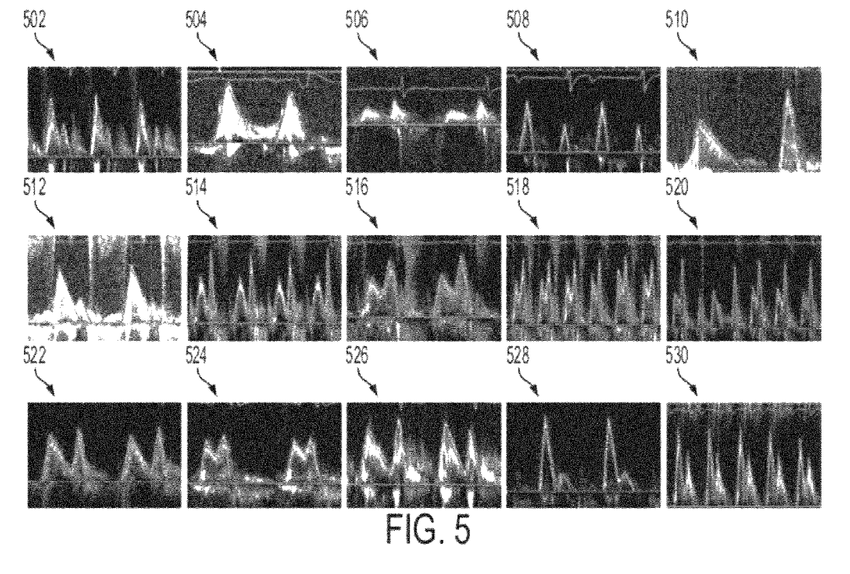
FIG. 5 illustrates exemplary segmentation results of MI patterns using the method of FIG. 2.

FIG. 5 illustrates exemplary segmentation results of MI patterns using the method of FIG. 2. As illustrated in FIG. 5, images 502-530 show various MI patterns including overlapping and non-overlapping E and A-waves segmented using the method of FIG. 2, as described above.

Figure 6:
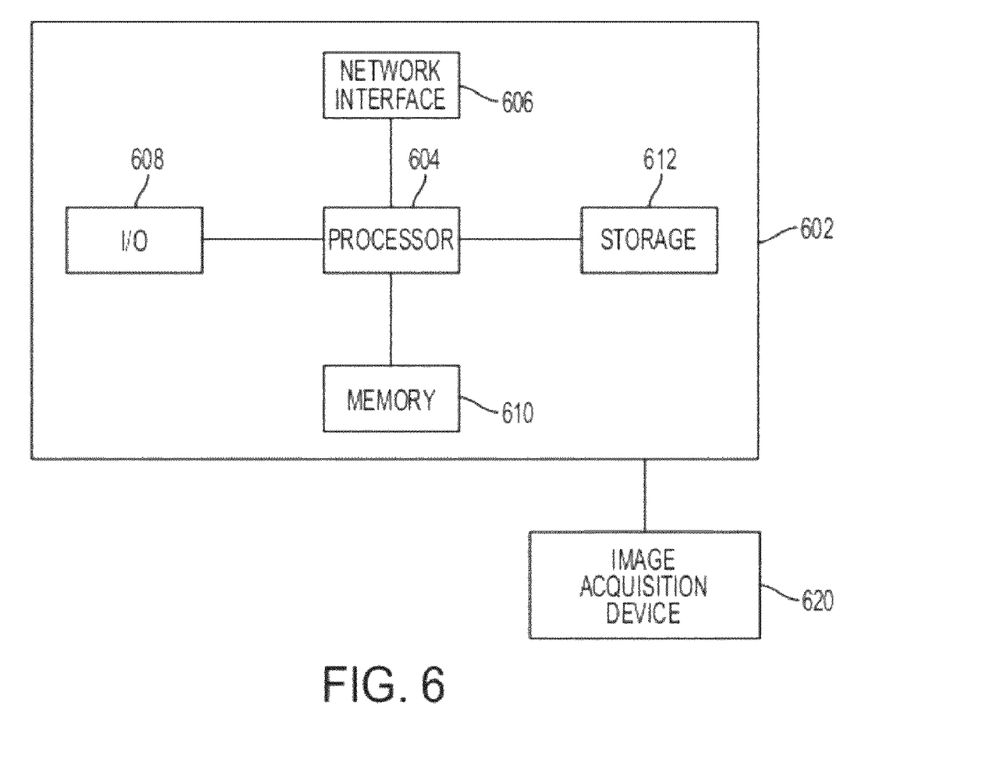
FIG. 6 is a high level block diagram of a computer capable of implementing the present invention.

The above-described methods for detection and segmentation of MI patterns in Doppler echocardiograms may be implemented on a computer using well-known computer processors, memory units, storage devices, computer software, and other components. A high level block diagram of such a computer is illustrated in FIG. 6. Computer 602 contains a processor 604 which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the method of FIG. 2 may be defined by the computer program instructions stored in the memory 610 and/or storage 612 (or a computer readable medium) and controlled by the processor 604 executing the computer program instructions. An image acquisition device 620, such as an ultrasound device, can be connected to the computer 602 to input the Doppler echocardiogram images to the computer 602. It is possible to implement the image acquisition device 620 and the computer 602 as one device. It is also possible that the image acquisition device 620 and the computer 602 communicate wirelessly through a network. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.) One skilled in the art will recognize that an implementation of an actual computer could contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for segmenting a mitral valve inflow (MI) pattern in a Doppler echocardiogram image, comprising:
   detecting left root candidates, right root candidates, and peak candidates in the image using trained root detectors;
   detecting single triangle candidates and double triangle candidates in the image based on the left root candidates, right root candidates, and peak candidates using trained global box detectors, wherein a detection probability is determined for each of the single triangle candidates and each of the double triangle candidates;
   determining a shape probability for each of the single triangle candidates and the double triangle candidates;
   selecting a best single triangle candidate based on the detection probabilities and shape probabilities of the single triangle candidates and a best double triangle candidate based on the detection probabilities and the shape probabilities of the double triangle candidates; and
   segmenting an MI pattern in the image by selecting one of the best single triangle candidate and the best double triangle candidate based on a shape probability comparison.

2. The method of claim 1, wherein said step of detecting left root candidates, right root candidates, and peak candidates in the image using trained root detectors comprises:
   detecting said left root candidates using a trained left root detector;
   detecting said right root candidates using a trained right root detector;
   detecting said peak candidates using a trained peak detector.

3. The method of claim 2, wherein each of said left root detector, said right root detector, and said peak detector is trained as a probabilistic boosting tree (PBT) based on training samples.

4. The method of claim 1, wherein said step of detecting single triangle candidates and double triangle candidates in the image based on the left root candidates, right root candidates, and peak candidates using trained global box detectors comprises:
   detecting said single triangle candidates using a trained single triangle detector, wherein each of said single triangle candidates is a combination of one of said left root candidates, one of said right root candidates, and one of said peak candidates; and
   detecting said double triangle candidates using a trained double triangle detector, wherein each of said double triangle candidates is a combination of one of said left root candidates, one of said right root candidates, and two of said peak candidates.

5. The method of claim 4, wherein each of said single triangle detector and said double triangle detector is trained as a probabilistic boosting tree (PBT) based on training samples.

6. The method of claim 4, wherein said step of detecting single triangle candidates and double triangle candidates in the image based on the left root candidates, right root candidates, and peak candidates using trained global box detectors further comprises:

estimating a location of an intersection between an E-wave and an A-wave in each of said double triangle candidates.

7. The method of claim 6, wherein said step of estimating a location of an intersection between an E-wave and an A-wave in each of said double triangle candidates comprises:

estimating said intersection in each of said double triangle candidates using a shape inference model.

8. The method of claim 1, wherein said step of determining a shape probability for each of the single triangle candidates and the double triangle candidates comprises:

determining a shape profile for each of the single triangle candidates and the double triangle candidates based on pixel intensity gradients along each of the single triangle candidates and each of the double triangle candidates.

9. The method of claim 1, further comprising:

determining whether said best single triangle candidate is an E-wave or an A-wave.

10. The method of claim 1, wherein said step of selecting a best single triangle candidate based on the detection probabilities and shape probabilities of the single triangle candidates and a best double triangle candidate based on the detection probabilities and the shape probabilities of the double triangle candidates comprises:

selecting one of said single triangle candidates that minimizes a fused probability that combines the detection probability and the shape probability; and selecting one of said double triangle candidates that minimizes a fused probability that combines the detection probability and the shape probability.

11. The method of claim 1, wherein said step of segmenting an MI pattern in the image by selecting one of the best single triangle candidate and the best double triangle candidate based on a shape probability comparison comprises:

selecting one of the best single triangle candidate and the best double triangle candidate having the highest shape probability.

12. The method of claim 1, further comprising:

automatically calculating at least one MI measurement based on the segmented MI pattern.

13. The method of claim 12, wherein said step of automatically calculating at least one MI measurement based on the segmented MI pattern comprises:

automatically calculating E-wave peak velocity, E-wave deceleration time, A-wave peak velocity, and A-wave duration.

14. An apparatus for segmenting a mitral valve inflow (MI) pattern in a Doppler echocardiogram image, comprising:

means for detecting left root candidates, right root candidates, and peak candidates in the image using trained root detectors;

means for detecting single triangle candidates and double triangle candidates in the image based on the left root candidates, right root candidates, and peak candidates using trained global box detectors, wherein a detection probability is determined for each of the single triangle candidates and each of the double triangle candidates;

means for determining a shape probability for each of the single triangle candidates and the double triangle candidates;

means for selecting a best single triangle candidate based on the detection probabilities and shape probabilities of the single triangle candidates and a best double triangle candidate based on the detection probabilities and the shape probabilities of the double triangle candidates; and means for segmenting an MI pattern in the image by selecting one of the best single triangle candidate and the best double triangle candidate based on a shape probability comparison.

15. The apparatus of claim 14, wherein said trained root detectors comprise a left root detector, a right root detector, and a peak detector, further comprising:

means for training each of said left root detector, said right root detector, and said peak detector as a probabilistic boosting tree (PBT) based on training samples.

16. The apparatus of claim 14, wherein said trained global box detectors comprise a single triangle detector for detecting said single triangle candidates and a double triangle detector for detecting said double triangle candidates, wherein each of said single triangle candidates is a combination of one of said left root candidates, one of said right root candidates, and one of said peak candidates, and wherein each of said double triangle candidates is a combination of one of said left root candidates, one of said right root candidates, and two of said peak candidates, further comprising:

means for training each of said single triangle detector and said double triangle detector as a probabilistic boosting tree (PBT) based on training samples.

17. The apparatus of claim 14, further comprising:

means for estimating a location of an intersection between an E-wave and an A-wave in each of said double triangle candidates.

18. The apparatus of claim 14, further comprising:

means for determining whether said best single triangle candidate is an E-wave or an A-wave.

19. The apparatus of claim 14, further comprising:

means for automatically calculating at least one MI measurement based on the segmented MI pattern.

20. The apparatus of claim 19, wherein said means for automatically calculating at least one MI measurement based on the segmented MI pattern comprises:

means for automatically calculating E-wave peak velocity, E-wave deceleration time, A-wave peak velocity, and A-wave duration.

21. A non-transitory computer readable medium encoded with computer executable instructions for segmenting a mitral valve inflow (MI) pattern in a Doppler echocardiogram image, the computer program instructions defining steps comprising:

detecting left root candidates, right root candidates, and peak candidates in the image using trained root detectors;

detecting single triangle candidates and double triangle candidates in the image based on the left root candidates, right root candidates, and peak candidates using trained global box detectors, wherein a detection probability is determined for each of the single triangle candidates and each of the double triangle candidates;

determining a shape probability for each of the single triangle candidates and the double triangle candidates;

selecting a best single triangle candidate based on the detection probabilities and shape probabilities of the single triangle candidates and a best double triangle candidate based on the detection probabilities and the shape probabilities of the double triangle candidates; and segmenting an MI pattern in the image by selecting one of the best single triangle candidate and the best double triangle candidate based on a shape probability comparison.

22. The non-transitory computer readable medium of claim 21, wherein the computer program instructions defining the step of detecting left root candidates, right root candidates, and peak candidates in the image using trained root detectors comprise computer program instructions defining the steps of:
  detecting said left root candidates using a trained left root detector;
  detecting said right root candidates using a trained right root detector;
  detecting said peak candidates using a trained peak detector.

23. The non-transitory computer readable medium of claim 21, wherein the computer program instructions defining the step of detecting single triangle candidates and double triangle candidates in the image based on the left root candidates, right root candidates, and peak candidates using trained global box detectors comprise computer program instructions defining the steps of:
  detecting said single triangle candidates using a trained single triangle detector, wherein each of said single triangle candidates is a combination of one of said left root candidates, one of said right root candidates, and one of said peak candidates; and
  detecting said double triangle candidates using a trained double triangle detector, wherein each of said double triangle candidates is a combination of one of said left root candidates, one of said right root candidates, and two of said peak candidates.

24. The non-transitory computer readable medium of claim 23, wherein the computer program instructions defining the step of detecting single triangle candidates and double triangle candidates in the image based on the left root candidates, right root candidates, and peak candidates using trained global box detectors further comprise computer program instructions defining the step of:
  estimating a location of an intersection between an E-wave and an A-wave in each of said double triangle candidates.

25. The non-transitory computer readable medium of claim 21, wherein the computer program instructions defining the step of determining a shape probability for each of the single triangle candidates and the double triangle candidates comprise computer program instructions defining the step of:
  determining a shape profile for each of the single triangle candidates and the double triangle candidates based on pixel intensity gradients along each of the single triangle candidates and each of the double triangle candidates.

26. The non-transitory computer readable medium of claim 21, further comprising computer program instructions defining the step of:
  determining whether said best single triangle candidate is an E-wave or an A-wave.

27. The non-transitory computer readable medium of claim 21, wherein the computer program instructions defining the step of selecting a best single triangle candidate based on the detection probabilities and shape probabilities of the single triangle candidates and a best double triangle candidate based on the detection probabilities and the shape probabilities of the double triangle candidates comprise computer program instructions defining the steps of:
  selecting one of said single triangle candidates that minimizes a fused probability that combines the detection probability and the shape probability; and
  selecting one of said double triangle candidates that minimizes a fused probability that combines the detection probability and the shape probability.

28. The non-transitory computer readable medium of claim 21, wherein the computer program instructions defining the step of segmenting an MI pattern in the image by selecting one of the best single triangle candidate and the best double triangle candidate based on a shape probability comparison comprise computer program instructions defining the step of:
  selecting one of the best single triangle candidate and the best double triangle candidate having the highest shape probability.

29. The non-transitory computer readable medium of claim 21, further comprising computer program instructions defining the step of:
  automatically calculating at least one MI measurement based on the segmented MI pattern.

* * * * *